(12) United States Patent
Kuroyama et al.

(10) Patent No.: US 9,797,780 B2
(45) Date of Patent: Oct. 24, 2017

(54) CONTACT TYPE INTERNAL THERMOMETER

(71) Applicant: CITIZEN HOLDINGS CO., LTD., Tokyo (JP)

(72) Inventors: Yukio Kuroyama, Sayama (JP); Masato Tsuchida, Sayama (JP)

(73) Assignee: CITIZEN WATCH CO., LTD., Tokyo (JP)

( * ) Notice: Subject to any disclaimer, the term of this patent is extended or adjusted under 35 U.S.C. 154(b) by 490 days.

(21) Appl. No.: 14/389,381

(22) PCT Filed: Feb. 21, 2013

(86) PCT No.: PCT/JP2013/054377
§ 371 (c)(1),
(2) Date: Sep. 30, 2014

(87) PCT Pub. No.: WO2013/145968
PCT Pub. Date: Oct. 3, 2013

(65) Prior Publication Data
US 2015/0071325 A1    Mar. 12, 2015

(30) Foreign Application Priority Data

Mar. 30, 2012  (JP) ................ 2012-081613

(51) Int. Cl.
*G01K 7/22*   (2006.01)
*A61B 5/00*   (2006.01)
(Continued)

(52) U.S. Cl.
CPC .............. *G01K 7/22* (2013.01); *A61B 5/01* (2013.01); *A61B 5/683* (2013.01); *G01K 7/427* (2013.01);
(Continued)

(58) Field of Classification Search
CPC .............. A61B 2562/0271; A61B 5/01; G01K 13/002; G01K 7/16; G01K 13/00;
(Continued)

(56) References Cited

U.S. PATENT DOCUMENTS 4,174,065 A * 11/1979 Knauth ............... G01F 1/28
174/16.1
4,648,055 A   3/1987 Ishizaka et al.
(Continued)

FOREIGN PATENT DOCUMENTS

CN   1380536 A   11/2002
CN   1395478 A   2/2003
(Continued)

OTHER PUBLICATIONS

The partial translation of an OA for corresponding Chinese Patent Application No. 201380017368.2. dated Dec. 9, 015.
(Continued)

*Primary Examiner* — Peter Macchiarolo
*Assistant Examiner* — Anthony W Megna Fuentes
(74) *Attorney, Agent, or Firm* — Hubbs, Enatsky & Inoue PLLC

(57) ABSTRACT

Provided is a contact type internal thermometer including: a measurement surface that is brought into contact with a surface to be measured of a measurement object; a first temperature sensor stack including a first measurement surface side temperature sensor arranged on a measurement surface side, and a first back surface side temperature sensor arranged on a back surface side; a second temperature sensor stack including a second measurement surface side temperature sensor arranged on a measurement surface side, and a second back surface side temperature sensor arranged on a back surface side; and a controller configured to calculate an internal temperature of the measurement object based on
(Continued)

measurement results of the respective temperature sensors, in which the first back surface side temperature sensor and the second back surface side temperature sensor have different surface areas.

5 Claims, 5 Drawing Sheets

(51) Int. Cl.
*G01K 7/42* (2006.01)
*G01K 13/00* (2006.01)
*A61B 5/01* (2006.01)

(52) U.S. Cl.
CPC .... *G01K 13/002* (2013.01); *A61B 2562/0271* (2013.01)

(58) Field of Classification Search
CPC ............ G01K 7/22; G01K 7/02; G01K 1/143; G01K 1/16; G01N 25/00; G01M 99/002
USPC ....... 374/120, 121, 100, 163, 179, 185, 170; 702/130–131; 600/549
See application file for complete search history.

(56) References Cited

U.S. PATENT DOCUMENTS

| | | | |
|---|---|---|---|
| 5,392,031 A | 2/1995 | Toriumi et al. | |
| 5,473,629 A | 12/1995 | Muramoto | |
| 5,738,441 A | 4/1998 | Cambridge et al. | |
| 6,280,397 B1 | 8/2001 | Yarden et al. | |
| 6,383,144 B1 | 5/2002 | Mooney et al. | |
| 7,597,668 B2 | 10/2009 | Yarden | |
| 2002/0128568 A1 | 9/2002 | Mooney et al. | |
| 2002/0150143 A1 | 10/2002 | Tokita et al. | |
| 2002/0191675 A1 | 12/2002 | Tokita et al. | |
| 2005/0163190 A1 | 7/2005 | Tokita et al. | |
| 2005/0220170 A1 | 10/2005 | Tokita et al. | |
| 2006/0056487 A1* | 3/2006 | Kuroda .................. G01K 1/165 374/179 |
| 2007/0274370 A1 | 11/2007 | Niiyama et al. | |
| 2008/0045855 A1 | 2/2008 | Mooney et al. | |
| 2009/0022202 A1 | 1/2009 | Yamamoto et al. | |
| 2011/0021891 A1 | 1/2011 | Yokoyama et al. | |
| 2011/0243183 A1 | 10/2011 | Goto | |
| 2012/0083710 A1 | 4/2012 | Yarden | |
| 2014/0036956 A1 | 2/2014 | Goto | |
| 2014/0278201 A1 | 9/2014 | Shimizu | |

FOREIGN PATENT DOCUMENTS

| | | |
|---|---|---|
| CN | 101074893 A | 11/2007 |
| JP | 2004-177346 A | 6/2004 |
| JP | 2007-212407 A | 8/2007 |
| JP | 2008-076144 A | 4/2008 |
| JP | 2009-222543 A | 10/2009 |
| JP | 2009-236624 A | 10/2009 |
| JP | 2011-185819 A | 9/2011 |
| JP | 2011-215107 A | 10/2011 |
| JP | 4798280 B2 | 10/2011 |

OTHER PUBLICATIONS

The partial translation of OA for relating Patent Application No. JP2012-081616 dated Sep. 29, 2015.
Dengjin Zhou, et al, "Shanghai Measurement and Testing, Issue 4", Apr. 30, 2011, Method for Improving Reliability of Contac-Type SurfaceThermometre, pp. 46-48. Pertinent parts discussed in Partial Translation of the Office Action dated Dec. 17, 2015, relating CN application No. 201380017565.4.
Partial Translation of Office Action of Dec. 17, 2015, relating CN application No. 201380017565.4.
Office Action dated Jun. 29, 2017, for relating U.S. Appl. No. 14/389,382.

* cited by examiner

CONTACT TYPE INTERNAL THERMOMETER

CROSS REFERENCE TO RELATED APPLICATIONS

This application is a National Stage of International Application No. PCT/JP2013/054377 filed Feb. 21, 2013, claiming priority based on Japanese Patent Application No. 2012-081613 filed on Mar. 30, 2012. The contents of each of the above documents are incorporated herein by reference in their entirety.

TECHNICAL FIELD

The present invention relates to a contact type internal thermometer.

BACKGROUND ART

In various situations, there are demands for rapid, accurate, and convenient (that is, non-invasive) measurement of an internal temperature instead of a surface temperature of an object to be measured (hereinafter referred to as "measurement object"). Measurement of temperatures of biological bodies, including a human body, is a typical example of those demands. However, it is generally difficult to measure the internal temperature (sometimes referred to as deep/core body temperature, etc.) of the internal region of the biological body, that is, the temperature of the biological body in an internal region that is considered to be held substantially at a constant temperature due to blood flow. When the measurement object is a human body, holding a thermometer at a position where heat is not easily lost, such as under the tongue or arm, reading the thermometer after a thermal equilibrium state is attained between the thermometer and the human body, and then adopting the temperature read as the body temperature, is the common way often used. However, it takes a long time of about 5 minutes to 10 minutes to attain the thermal equilibrium state, and the obtained body temperature does not always match with the internal temperature of the human body. Therefore, it may be difficult to apply such a method to an object having difficulty in undergoing long-term body temperature measurement, such as babies and patients with a certain injury or disease. Further, it is difficult to obtain a body temperature with accuracy high enough for precise body temperature management.

In view of the above, as a thermometer for rapidly and accurately measuring the internal temperature of the human body, there has been proposed a thermometer including at least two sets of sensors each including a first temperature sensor that is brought into contact with the body surface, and a second temperature sensor arranged so as to oppose the first temperature sensor across a heat insulating member. In such a thermometer, a system of heat conduction equations is solved based on the temperature measurement results of the respective temperature sensors in a steady state to obtain the internal temperature. Therefore, the thermometer is designed so that magnitudes of heat fluxes passing through the respective sets differ from each other.

For example, in JP 2007-212407 A, there is disclosed a thermometer in which a thermal resistance value of the heat insulating member differs for each sensor set.

Further, in JP 4798280 B, there is disclosed a thermometer in which a heat insulating member is further arranged between the second temperature sensor (intermediate sensor) and outside air so that a thermal resistance value of the heat insulating member differs for each sensor set.

Further, in JP 2008-76144 A, there is disclosed a thermometer in which a heatsink having a different area is arranged between the second temperature sensor (temperature measuring means 21, 22) and outside air for each sensor set.

SUMMARY OF INVENTION

Technical Problem

In the above-mentioned thermometer described in Patent Literature 1, in order to achieve difference in thermal resistance value of the heat insulating member interposed between the first temperature sensor and the second temperature sensor for each set, it is necessary to mold an appropriate material for the heat insulating member with high accuracy, and to accurately mount the temperature sensors to the heat insulating member. Further, in the above-mentioned thermometers described in Patent Literatures 2 and 3, it is necessary to thermally accurately mount the heat insulating members made of different materials and the heatsinks having different shapes between the second temperature sensors and the outside air. Both of those designs cause increase in time and cost in terms of manufacture.

The present invention has been made in view of the above-mentioned circumferences, and has an object to easily achieve, in a contact type internal thermometer, difference in magnitude of heat fluxes passing through a plurality of sets of first temperature sensors and second temperature sensors arranged across heat insulating members.

Note that the description so far mainly concerns a thermometer for measuring the internal temperature of the human body as a typical example of the contact type internal thermometer. However, the contact type internal thermometer according to the present invention is not limited thereto, and is applicable to any measurement object that requires measurement of its internal temperature in a non-invasive manner, regardless of whether it is living or non-living matter.

Solution to Problem

In order to achieve the above-mentioned object, the invention disclosed in this application has various aspects, and typical aspects are summarized in the following.

(1) A contact type internal thermometer includes: a measurement surface that is brought into contact with a surface to be measured of a measurement object so as to calculate an internal temperature of the measurement object; a first temperature sensor stack including a first measurement surface side temperature sensor arranged on a measurement surface side of a first flexible printed board, and a first back surface side temperature sensor arranged on a back surface side of the first flexible printed board; a second temperature sensor stack including a second measurement surface side temperature sensor arranged on a measurement surface side of a second flexible printed board, and a second back surface side temperature sensor arranged on a back surface side of the second flexible printed board; and a controller configured to calculate the internal temperature of the measurement object based on measurement results of the first measurement surface side temperature sensor, the first back surface side temperature sensor, the second measurement surface side temperature sensor, and the second back surface side temperature sensor, in which the first back surface side temperature sensor and the second back surface side temperature sensor have different surface areas.

(2) In the contact type internal thermometer according to the aspect (1), the first back surface side temperature sensor and the second back surface side temperature sensor have different volumes.

(3) In the contact type internal thermometer according to the aspect (1) or (2), the first back surface side temperature sensor has a larger volume than a volume of the first measurement surface side temperature sensor.

(4) The contact type internal thermometer according to any one of the aspects (1) to (3) further includes a cooling mechanism configured to cool the first temperature sensor stack and the second temperature sensor stack after the internal temperature is calculated by the controller.

Advantageous Effects of Invention

According to the above-mentioned aspects (1) and (2), in the contact type internal thermometer, it is possible to easily achieve difference in magnitude of the heat fluxes passing through the plurality of sets of the first temperature sensors and the second temperature sensors arranged across the heat insulating members.

According to the above-mentioned aspect (3), it is possible to increase the temperature difference between the first measurement surface side temperature sensor and the first back surface side temperature sensor in the first temperature sensor stack.

According to the above-mentioned aspect (4), it is possible to measure the internal temperature of the measurement object accurately each time during successive measurements.

DESCRIPTION OF EMBODIMENT

Now, an embodiment of the present invention is described in detail with reference to the drawings.

Figure 1:
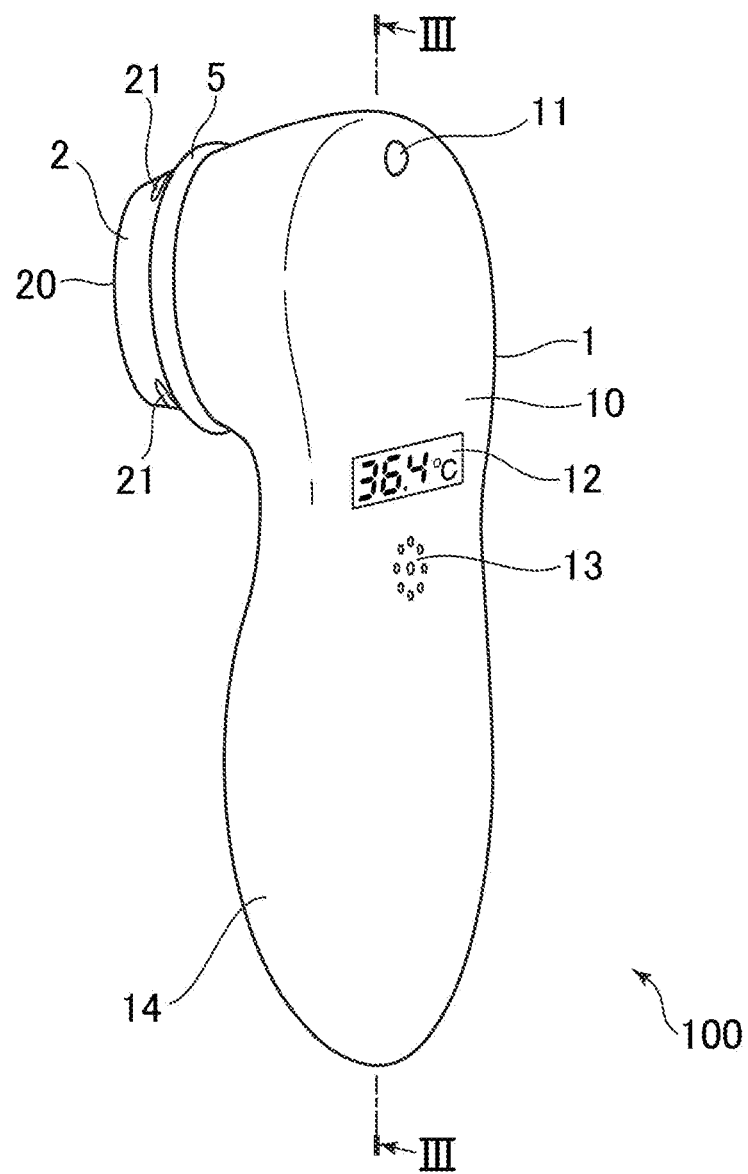
FIG. 1 is an external view of a contact type internal thermometer according to an embodiment of the present invention as viewed from a back surface side thereof.
Figure 2:
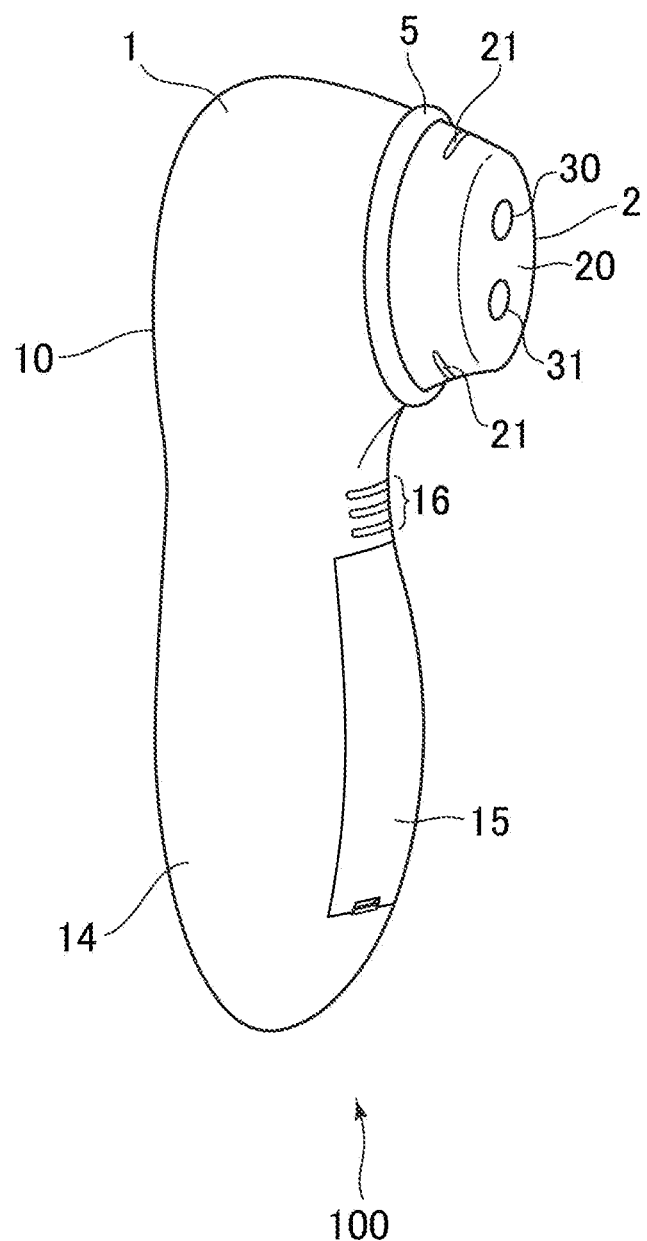
FIG. 2 is an external view of the contact type internal thermometer according to the embodiment of the present invention as viewed from a measurement surface side thereof.

FIG. 1 is an external view of a contact type internal thermometer 100 according to the embodiment of the present invention as viewed from a back surface side thereof, and FIG. 2 is an external view of the contact type internal thermometer 100 according to the same embodiment as viewed from a measurement surface side thereof. Note that in this specification, the contact type internal thermometer means a thermometer that is brought into contact with a surface of a measurement object to measure an internal temperature thereof. Further, the internal temperature means not a surface temperature of the measurement object, but a temperature of a part inside the measurement object, which is substantially considered to be a constant-temperature heat source. Note that, "substantially considered to be a constant-temperature heat source" means that, as in the case where the heat capacity inside the measurement object is large or as a result of constant supply of heat inside the measurement object, it is considered that measurement by the contact type internal thermometer does not affect the temperature in practical use. For example, when the measurement object is a biological body, heat is constantly supplied from the trunk due to blood flow, which corresponds to the latter case.

The contact type internal thermometer 100 described in this embodiment is a portable type thermometer as illustrated in the drawings, and has a measurement head 2 mounted on a leading end of a case 1. The measurement head 2 is provided so as to protrude from the case 1, and the leading end thereof is formed into a substantially flat measurement surface 20. The measurement surface 20 is brought into contact with a surface to be measured of the measurement object, for example, the skin, to thereby measure its internal temperature. On the measurement surface 20, as illustrated in FIG. 2, a first probe 30 and a second probe 31 each having a substantially circular shape are arranged in series along the longitudinal direction of the contact type internal thermometer 100. Note that arrangement of those first probe 30 and second probe 31 is arbitrary, and the arrangement direction may not necessarily be the longitudinal direction of the contact type internal thermometer 100.

In a back surface 10 of the case 1, which is a surface on the opposite side to the measurement surface 20, a lamp 11, a display 12, and a buzzer 13 are provided. In this specification, a direction in which the measurement surface 20 is directed is hereinafter referred to as a measurement surface side, and a direction in which the back surface is directed, which is opposite to the measurement surface side, is hereinafter referred to a back surface side. Further, the case 1 has a long and rounded shape, and has a grip 14 to be held by a user. As seen in FIG. 2, a battery case lid 15 is provided on the measurement surface side of the grip 14 of the case 1, and a battery can be accommodated therein as a power source for the contact type internal thermometer 100. Further, an intake hole 16 is formed at an appropriate position of the case 1, which corresponds to the position illustrated in FIG. 2 in this case, and an exhaust hole 21 is formed through a side surface of the measurement head 2. Thus, internal spaces of the case 1 and the measurement head 2 are communicated to outside air. The case 1 and the measurement head 2 are connected to each other by a support ring 5.

Note that FIGS. 1 and 2 illustrate an example of the design of the contact type internal thermometer 100. The design may be appropriately changed with consideration of the main application, marketability, and the like. Further, the arrangement of the respective components may be arbitrarily selected within a range that does not affect the function.

Figure 3:
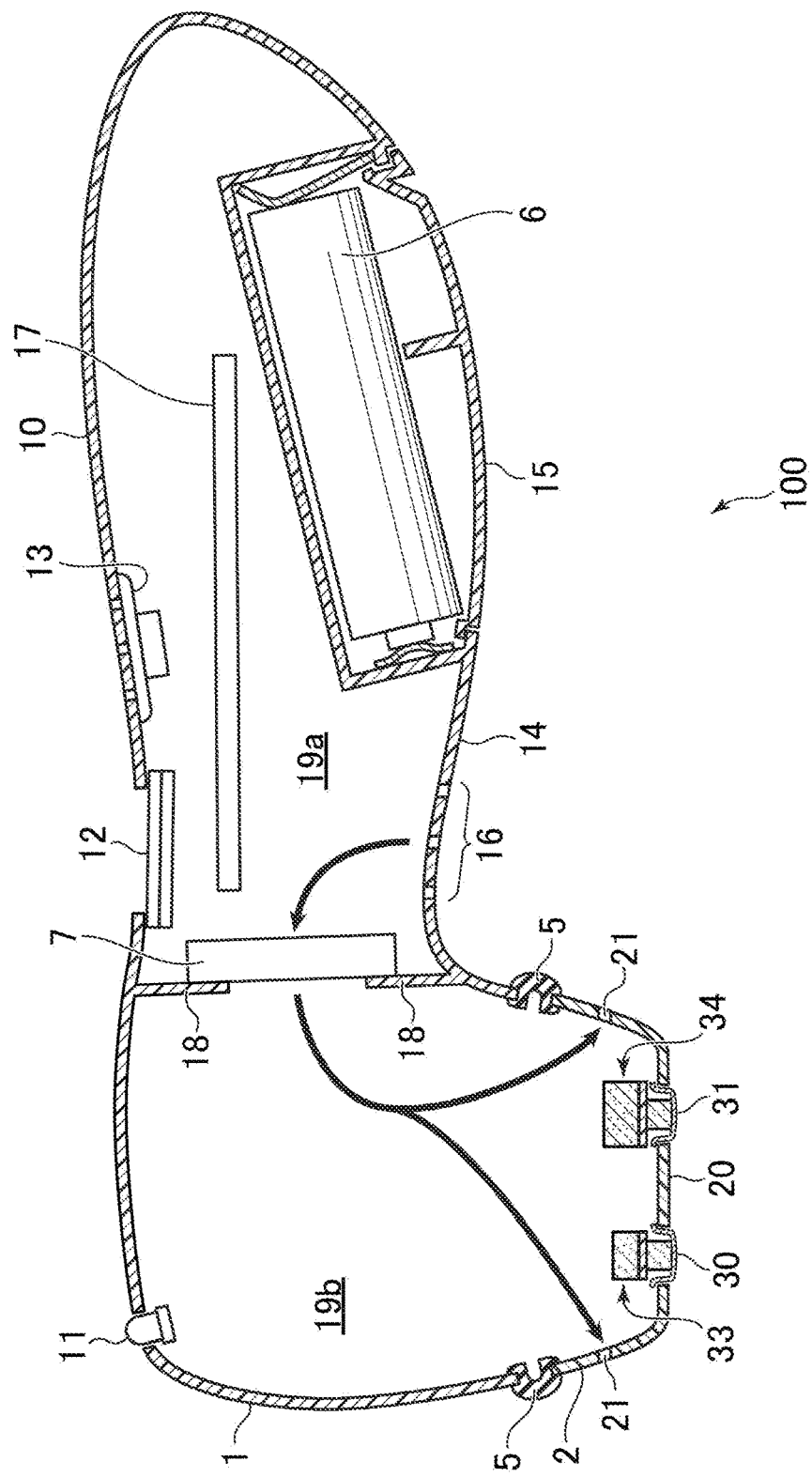
FIG. 3 is a schematic sectional view of the contact type internal thermometer taken along the line III-III of FIG. 1.

FIG. 3 is a schematic sectional view of the contact type internal thermometer 100 taken along the line III-III of FIG. 1. The case 1 is a hollow molded product made of an arbitrary synthetic resin, preferably an ABS resin, and various components of the contact type internal thermometer 100 are integrally accommodated inside the case 1. Inside the grip 14, a battery 6 and a circuit board 17 are accommodated. The circuit board 17 has various electronic components such as a controller (not shown) mounted thereon, which are supplied with power from the battery 6 so as to supply power to all components that require power and to control the operation thereof. The battery 6 illustrated in FIG. 3 is a commercially available AAA dry cell, but the form thereof may be arbitrary. The shape of the battery 6 is arbitrary, such as a button type or a square type, and also the selection of a primary cell or a secondary cell is arbitrary. Note that wiring for electrically connecting each component to the circuit board 17 is omitted in order to simplify the illustration.

The lamp 11 is preferred to be a light emitting diode capable of emitting a plurality of colors of light, and is turned on to notify the user of the state of the contact type internal thermometer 100. The display 12 is a liquid crystal display device in this embodiment, and notifies the user of the measurement result of the contact type internal thermometer 100 in a mode as illustrated in FIG. 1. As a matter of course, the display 12 may display other arbitrary information, such as a remaining amount of the battery 6. Alternatively, the display 12 may simultaneously display the state of the contact type internal thermometer 100 making it possible to omit the lamp 11. The buzzer 13 is a general electronic buzzer in this embodiment, and notifies the user of the state of the contact type internal thermometer 100 by a beep sound. Note that the type of the buzzer 13 is also arbitrary, and the buzzer 13 may be equipped with a speaker for notification by voice or a melody. Alternatively, notification may be given only by the lamp 11 and/or the display 12, and the buzzer 13 may be omitted.

Further, a partition wall 18 is provided inside the case 1, which partitions the inside of the case 1 into a grip space 19a and a head space 19b. The partition wall 18 has an opening formed therein, and a blower 7 is mounted so as to close the opening. The function of the blower 7 is described later.

The measurement head 2 is mounted on the leading end portion of the case 1 through intermediation of the support ring 5. The support ring 5 is made of a material having elasticity and excellent heat insulating properties, preferably silicon rubber or foam thereof. The support ring 5 allows a slight movement of the measurement head 2 with respect to the case 1, and blocks heat from transmitting from the measurement head 2 to the case 1. This is for reliably bringing the measurement surface 20 into close contact with the measurement object when the measurement surface 20 is brought into contact with the measurement object, and for preventing occurrence of measurement error due to outflow of heat from the measurement head 2 to the case 1. However, the support ring 5 is not always necessary. When there is no problem in close contact between the measurement surface 20 and the measurement object and when the measurement head 2 is made of a material having a sufficiently low thermal conductivity and hence has no problem in practical use, the support ring 5 may be omitted. The measurement head 2 may be directly fixed to the case 1, or the measurement head 2 and the case 1 may be integrally formed. Further, the shape of the support ring 5 is not limited to a ring shape, and a member having an arbitrary shape may be used.

The measurement head 2 is preferred to be made of a material having a stable shape, a low thermal conductivity, and a small specific heat. For example, hard urethane foam and hard vinyl chloride foam are suitably used. However, also in this case, the material is not particularly limited if there is no problem in practical use, and the material may be arbitrary.

The measurement surface 20 of the measurement head 2 has openings formed at positions corresponding to the respective first probe 30 and second probe 31, and each probe is mounted so as to slightly protrude from the measurement surface 20. Each probe is preferred to be made of a material having a high thermal conductivity, and is made of a metal in this embodiment. Note that each probe is preferred to be made of a material having a corrosion resistance property, and aluminum and stainless steel are suitable among metal materials. Note that as described above, the measurement head 2 itself is made of a material having a low thermal conductivity, and hence the first probe 30 and the second probe 31 are thermally separated from each other.

A first temperature sensor stack 33 is provided on the back surface side of the first probe 30, and the first temperature sensor stack 33 and the first probe 30 are thermally coupled to each other. Further, a second temperature sensor stack 34 is provided on the back surface side of the second probe 31, and the second temperature sensor stack 34 and the second probe 31 are thermally coupled to each other. The first temperature sensor stack 33 and the second temperature sensor stack 34 are described in detail later. Note that in this embodiment, two temperature sensor stacks, that is, the first temperature sensor stack 33 and the second temperature sensor stack 34. are provided, but three or more probes and three or more temperature sensor stacks may be provided for the purpose of mutual error compensation or for backup in the event of failure.

Figure 4:
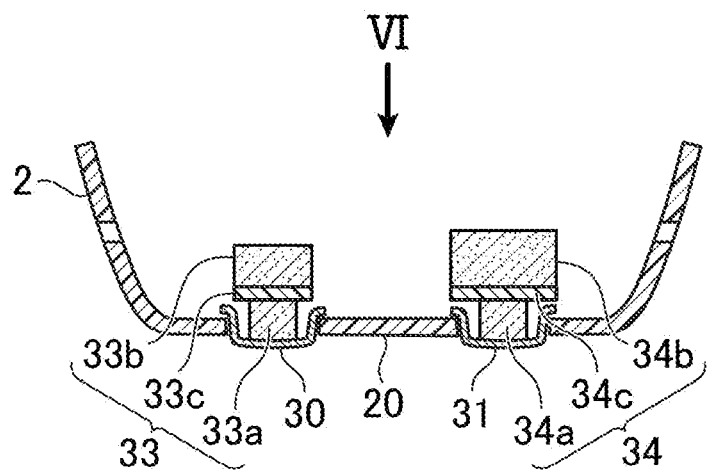
FIG. 4 is an enlarged sectional view of the vicinity of a measurement head in FIG. 3.

FIG. 4 is an enlarged sectional view of the vicinity of the measurement head 2 in FIG. 3. FIG. 4 omits the illustration of members located on the back surface side with respect to the support ring 5 of FIG. 3.

As illustrated in detail in FIG. 4, the first temperature sensor stack 33 has a structure of stacking a first measurement surface side temperature sensor 33a that is arranged on the measurement surface side so as to be brought into contact and thermally coupled with the first probe 30, a first back surface side temperature sensor 33b arranged on the back surface side, and a first flexible printed board 33c arranged between the first measurement surface side temperature sensor 33a and the first back surface side temperature sensor 33b, so as to mount those temperature sensors on both surfaces of the first flexible printed board 33c. Note that the first flexible printed board 33c functions as a thermal resistor for forming a heat flow path from the first measurement surface side temperature sensor 33a to the first back surface side temperature sensor 33b.

Further, the second temperature sensor stack 34 has a structure similar to that of the first temperature sensor stack 33, that is, a structure of stacking a second measurement surface side temperature sensor 34a arranged on the measurement surface side so as to be brought into contact and thermally coupled with the second probe 31, a second back surface side temperature sensor 34b arranged on the back surface side, and a second flexible printed board 34c arranged between the second measurement surface side temperature sensor 34a and the second back surface side temperature sensor 34b, so as to mount those temperature sensors on both surfaces of the second flexible printed board 34c. Also the second flexible printed board 34c functions as a thermal resistor for forming a heat flow path from the second measurement surface side temperature sensor 34a to the second back surface side temperature sensor 34b.

Therefore, when the measurement surface 20 is brought into contact with the measurement object, heat from the measurement object is transmitted to the first probe 30 and the second probe 31. In the first temperature sensor stack 33, the heat passes through the first measurement surface side temperature sensor 33a, the first flexible printed board 33c, and the first back surface side temperature sensor 33b in the stated order, and in the second temperature sensor stack 34, the heat passes through the second measurement surface side temperature sensor 34a, the second flexible printed board 34c, and the second back surface side temperature sensor 34b in the stated order. Then, the heat is dissipated to the atmosphere.

Any temperature sensor may be used for each temperature sensor, but a thermistor is used in this embodiment. Each temperature sensor is connected to the circuit board 17 (see FIG. 3) via wiring (not shown) so that the temperature in each temperature sensor can be detected.

The important thing here is that, in a steady state, a heat flux passing through the first temperature sensor stack 33 is different from a heat flux passing through the second temperature sensor stack 34. That is, the first temperature sensor stack 33 and the second temperature sensor stack 34 are formed so that when the same temperature difference is applied to both ends thereof, the heat fluxes passing through the respective temperature sensor stacks are different from each other. As a method of achieving difference in heat fluxes passing through the first temperature sensor stack 33 and the second temperature sensor stack 34 as described above, in this embodiment, the first back surface side temperature sensor 33b and the second back surface side temperature sensor 34b are formed to have different surface areas. Further, along therewith, the first back surface side temperature sensor 33b and the second back surface side temperature sensor 34b have different volumes.

This point is described with reference to the first temperature sensor stack 33 illustrated in FIG. 4. The heat from the measurement object is transmitted through the first probe 30 to the first measurement surface side temperature sensor 33a, passes through the first flexible printed board 33c to flow into the first back surface side temperature sensor 33b, and is dissipated to the atmosphere. At this time, as illustrated in FIG. 4, when the volume and the surface area exposed to outside air of the first back surface side temperature sensor 33b are larger than those of the first measurement surface side temperature sensor 33a, the dissipated amount of heat increases. Therefore, compared to a case where a temperature sensor having the same shape as the first measurement surface side temperature sensor 33a is used as the first back surface side temperature sensor 33b, the heat flux increases, and the temperature difference between the first measurement surface side temperature sensor 33a and the first back surface side temperature sensor 33b increases. In contrast, when the volume and the surface area exposed to outside air of the first back surface side temperature sensor 33b are smaller than those of the first measurement surface side temperature sensor 33a, the amount of heat dissipated to the atmosphere reduces. Thus, the heat flux may decrease and the temperature difference between the first measurement surface side temperature sensor 33a and the first back surface side temperature sensor 33b may decrease.

That is, when there is a difference in combination of sizes of the temperature sensors forming each of the first temperature sensor stack 33 and the second temperature sensor stack 34, as a matter of course, the magnitudes of the heat fluxes passing through the first temperature sensor stack 33 and the second temperature sensor stack 34 differ from each other. Further, the characteristic to be affected by the magnitude difference is the characteristic of heat dissipation to the outside air. Therefore, the surface area or volume may be used as a specific value for evaluating the size of the temperature sensor. Further, as the surface area, to be precise, a total value of areas of parts exposed to the outside air may be employed. However, there is no problem in practical use even when the surface area of the temperature sensor is simply employed for convenience.

Note that although not particularly limited, in this embodiment, the first flexible printed board 33c and the second flexible printed board 34c are made of the same material having the same thickness. This is because the same sheet may be cut out to obtain the first flexible printed board 33c and the second flexible printed board 34c, which is advantageous in terms of manufacture. The materials of the first flexible printed board 33c and the second flexible printed board 34c are not particularly limited, and may be generally-used polyimide or the like.

Now, the principle of measuring the internal temperature by the contact type internal thermometer 100 of this embodiment is described with reference to FIG. 5.

Figure 5:
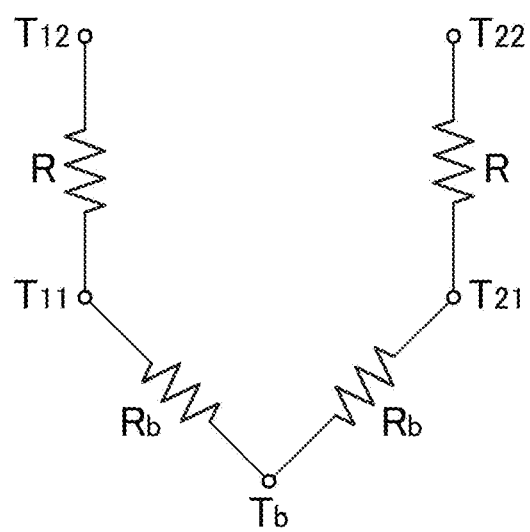
FIG. 5 is a thermal equivalent circuit diagram of a measurement section provided in the measurement head of the contact type internal thermometer according to the embodiment of the present invention.

FIG. 5 is a thermal equivalent circuit diagram of a measurement section provided in the measurement head 2 of the contact type internal thermometer 100 according to this embodiment. FIG. 5 is described with reference to FIG. 4. $T_b$ represents an internal temperature of the measurement object, $T_{11}$ represents a temperature of the first measurement surface side temperature sensor 33a, $T_{12}$ represents a temperature of the first back surface side temperature sensor 33b, $T_{21}$ represents a temperature of the second measurement surface side temperature sensor 34a, and $T_{22}$ represents a temperature of the second back surface side temperature sensor 34b. Further, a heat resistance $R_b$ is a heat resistance when heat transmits from the inside of the measurement object through the first probe 30 and the second probe 31 to the first measurement surface side temperature sensor 33a and the second measurement surface side temperature sensor 34a, and a heat resistance R is a heat resistance of each of the first flexible printed board 33c and the second flexible printed board 34c. Further, $T_b > T_{11} > T_{12}$ and $T_b > T_{21} > T_{22}$ are satisfied.

When it is assumed that the illustrated system is in a steady state, a heat flux flowing from $T_b$ to $T_{12}$ is constant, and hence the following expression is satisfied.

$$\frac{(T_{11} - T_{12})}{R} = \frac{(T_b - T_{11})}{R_b} \qquad \text{[Math. 1]}$$

Similarly, considering a heat flux flowing from $T_b$ to $T_{22}$, the following expression is satisfied.

$$\frac{(T_{21} - T_{22})}{R} = \frac{(T_b - T_{21})}{R_b} \qquad \text{[Math. 2]}$$

Based on Expressions 1 and 2, the internal temperature $T_b$ is obtained as follows.

$$T_b = \frac{T_{21}(T_{11} - T_{12}) - T_{11}(T_{21} - T_{22})}{(T_{11} - T_{12}) - (T_{21} - T_{22})} \qquad \text{[Math. 3]}$$

Referring to Expression 3, Expression 3 includes a difference $(T_{11}-T_{12})$ between measured values of the first measurement surface side temperature sensor 33a and the first back surface side temperature sensor 33b, a difference $(T_{21}-T_{22})$ between measured values of the second measurement surface side temperature sensor 34a and the second back surface side temperature sensor 34b, and a difference $(T_{11}-T_{12})-(T_{21}-T_{22})$ of those differences. This means that as the temperature difference between the first measurement surface side temperature sensor 33a and the first back surface side temperature sensor 33b, the temperature difference between the second measurement surface side temperature sensor 34a and the second back surface side temperature sensor 34b, and the difference between those temperature differences increase, the measurement result can be obtained with higher accuracy.

The level of measurement accuracy is discussed, which depends on the combination of the temperature sensors having different sizes.

Figure 6:
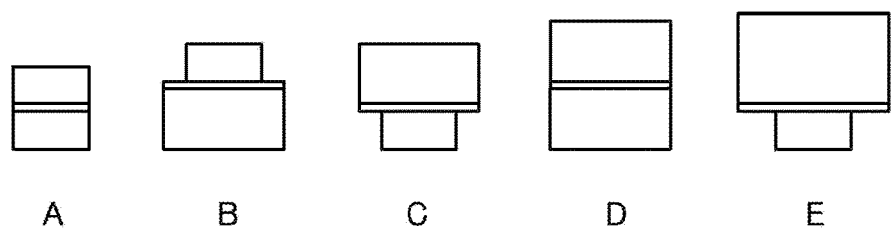
FIG. 6 is a view illustrating examples of temperature sensor stacks, each obtained by combining temperature sensors having different sizes.

FIG. 6 is a view illustrating examples of temperature sensor stacks each obtained by combining temperature sensors having different sizes. FIG. 6 illustrates five types (A to E) of temperature sensor stacks each including the measurement surface side temperature sensor on the lower side and the back surface side temperature sensor on the upper side. As the temperature sensors, thermistors of three sizes (large, medium, and small) are prepared, and each of the temperature sensor stacks A to E is a combination thereof. The size of each thermistor is as follows.

Large: width 2.0 mm/height 1.2 mm/depth 1.2 mm
Medium: width 1.6 mm/height 0.8 mm/depth 0.8 mm
Small: width 1.0 mm/height 0.5 mm/depth 0.5 mm Further, the combination of thermistors in each temperature sensor stack is as follows.

Figure 7:
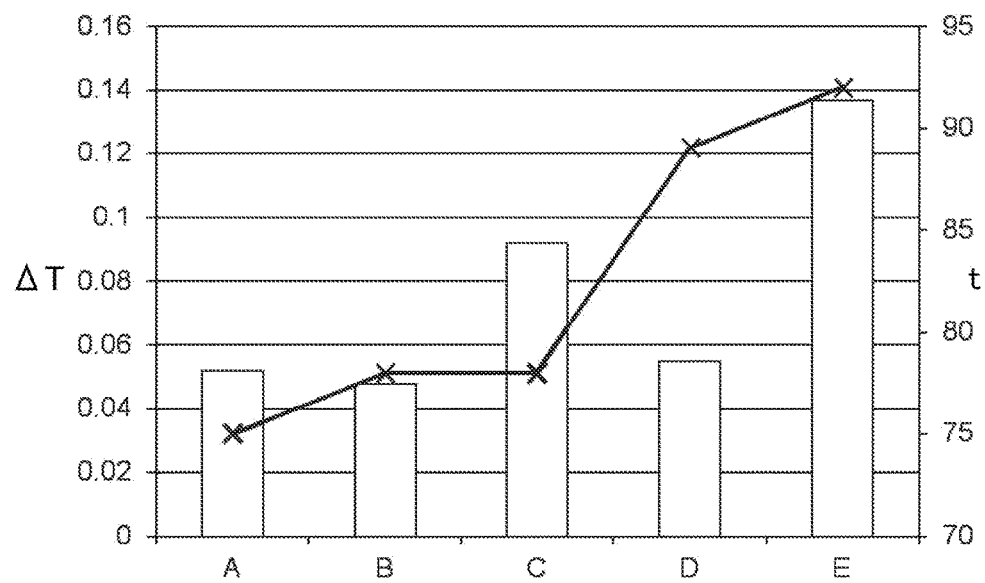
FIG. 7 is a graph showing a time until each temperature sensor stack illustrated in FIG. 6 reaches a steady state, and a temperature difference between a measurement surface side temperature sensor and a back surface side temperature sensor in the steady state.

A: measurement surface side, small/back surface side, small
B: measurement surface side, medium/back surface side, small
C: measurement surface side, small/back surface side, medium
D: measurement surface side, medium/back surface side, medium
E: measurement surface side, small/back surface side, large FIG. 7 is a graph showing a time until each temperature sensor stack illustrated in FIG. 6 reaches a steady state, and a temperature difference between the measurement surface side temperature sensor and the back surface side temperature sensor in the steady state. Note that in the same graph, a line chart represents a time t required to reach the steady state, and a bar chart represents a temperature difference ΔT between the measurement surface side temperature sensor and the back surface side temperature sensor in the steady state.

Note that the graph shown in FIG. 7 is obtained through simulation by a computer assuming that each temperature sensor stack is placed under an environment with an outside air temperature of 25° C., and the measurement surface side temperature sensor is brought into contact with skin whose internal temperature is 37° C.

The time t increases as the size of the thermistor used in each temperature sensor stack increases, which is considered to be because the heat capacity of the temperature sensor stack increases and hence it takes time to heat the temperature sensor stack until the temperature sensor stack reaches the steady state. On the other hand, the temperature difference ΔT is slightly smaller in (B) in which the back surface side temperature sensor is small compared to (A) in which the sizes of the measurement surface side temperature sensor and the back surface side temperature sensor are both equally small. Further, in (D) in which the sizes of the measurement surface side temperature sensor and the back surface side temperature sensor are both equally medium, the temperature difference ΔT increases slightly but shows little change. In contrast, in (C) in which the back surface side sensor is large, the temperature difference ΔT increases markedly, and in (E) in which the back surface side sensor is larger, the temperature difference ΔT increases further. Based on the above, it is understood that the temperature sensor stack in which the size of the back surface side temperature sensor is larger than the size of the measurement surface side temperature sensor has an increased temperature difference ΔT therebetween, which contributes to increase in accuracy of the measurement result. Further, based on the point of difference between the temperature differences of the two sets of temperature sensor stacks, among the temperature sensor stacks of A to E given here, two of three types of temperature sensor stacks of one of A, B, and D, C, and E may be used.

The combination of the sizes of the temperature sensors to be actually used as the temperature sensor stack may be selected considering the time required to reach the steady state, the measurement accuracy, and other factors. However, based on the study represented in FIGS. 6 and 7, a stack in which the size of the first back surface side temperature sensor 33b is larger than the size of the first measurement surface side temperature sensor 33a may be selected as the first temperature sensor stack 33, and a stack in which the size of the second back surface side temperature sensor 34b is larger than the size of the second measurement surface side temperature sensor 34a, and the size of the second back surface side temperature sensor 34b differs from the size of the first back surface side temperature sensor 33b, may be selected as the second temperature sensor stack 34. In this manner, higher measurement accuracy can be obtained, and the measurement time may be suitable for practical use. As such a combination, a combination of C and E illustrated in FIG. 6 is preferred. Note that in the measurement head illustrated in FIG. 4, C is employed as the first temperature sensor stack 33, and E is employed as the second temperature sensor stack 34.

Subsequently, the procedure of measuring the internal temperature by using the contact type internal thermometer 100 according to this embodiment, that is, the procedure of the temperature measurement operation is described with reference to FIGS. 1 to 4.

Procedure 1: the measurement surface 20 of the contact type internal thermometer 100 is brought into contact with the measurement object.

Procedure 2: the temperature measurement operation is started by the controller mounted on the circuit board 17. Note that the temperature measurement operation may be automatically started by detecting increase of the temperature to be measured by the first measurement surface side temperature sensor 33a or the second measurement surface side temperature sensor 34a, or may be started in response to the user's operation of a switch such as a push button (not shown). At this time, the controller notifies the user of the start of the measurement by a beep sound using the buzzer 13. Simultaneously, the lamp 11 is turned on in an arbitrary color, for example, red, so as to urge the user to maintain the measurement surface 20 in a contact state with the measurement object.

Procedure 3: after the first temperature sensor stack 33 and the second temperature sensor stack 34 reach the steady state, the controller calculates and displays the internal temperature of the measurement object. That is, the controller monitors the outputs of the first measurement surface side temperature sensor 33a, the first back surface side temperature sensor 33b, the second measurement surface side temperature sensor 34a, and the second back surface side temperature sensor 34b. When the controller detects that the temperature changes of those temperature sensors are equal to or less than preset thresholds, the internal temperature is obtained based on Expression 3 with use of the outputs from those temperature sensors. Therefore, the controller calculates the internal temperature of the measurement object based on the measurement results of the first measurement surface side temperature sensor 33a, the first back surface side temperature sensor 33b, the second measurement surface side temperature sensor 34a, and the second back surface side temperature sensor 34b.

The controller causes the display 12 to display the internal temperature calculated as described above as illustrated in FIG. 1. Further, by generating the beep sound using the buzzer 13, and turning on the lamp 11 in an arbitrary color different from the previous color, for example, green, the user is notified of the end of the measurement. Note that the user is notified of the calculated internal temperature through display on the display 12 in this embodiment, but the present invention is not limited thereto. The results may be accumulated in a memory of the contact type internal thermometer 100, or may be output through wired or wireless connection to an external device of the contact type internal thermometer 100. In this case, the display 12 is not always necessary.

Note that in the description above, various notifications of measurement start and measurement end are given to the user through the beep sound using the buzzer 13 and the turning-on of the lamp 11, but notification methods therefor are not limited to those exemplified above. In particular, the beep sound may be omitted, or may be turned off in response to the setting by the user. It may be preferred to give various notifications to the user through only the turning-on of the lamp 11 without using the sound, such as when the measurement object is a sleeping infant, because measurement can be established without interrupting the sleep of the infant. As a matter of course, how to turn on the lamp 11, for example, the selection of the emission color, is arbitrary. Further, independently of the emission color, the lamp 11 may be caused to flash, the intensity of the emitted light may be changed, or a plurality of lamps 11 may be provided to change the number or position of the turned-on lamps, to thereby give various notifications to the user. Further, as described above, various notifications may be given to the user using not the lamp 11 but the display 12.

Procedure 4: the controller activates the blower 7 to cool the measurement section. Through this operation, the first temperature sensor stack 33 and the second temperature sensor stack 34 are cooled to prepare for the next measurement. For example, considering a case where an internal temperature of a measurement object having a relatively high temperature is measured first, and immediately thereafter an internal temperature of a measurement object having a relatively low temperature is successively measured, at the time of the first measurement, the temperatures of the first temperature sensor stack 33 and the second temperature sensor stack 34 may increase to be higher than a temperature necessary for the next measurement. At this time, in order to achieve a steady state in the first temperature sensor stack 33 and the second temperature sensor stack 34, it is required to wait for natural cooling of those members through heat dissipation, which may take time for the measurement. Therefore, the first temperature sensor stack 33 and the second temperature sensor stack 34 are cooled to some degree at each time of measurement.

In this embodiment, the blower 7 generates an air flow that flows from the grip space 19a toward the head space 19b of FIG. 1. Therefore, as indicated by the arrow in FIG. 3, the air flow is induced by the blower 7 to be taken in through the intake hole 16, pass through the blower 7, pass the vicinity of the first temperature sensor stack 33 and the second temperature sensor stack 34, and be exhausted through the exhaust hole 21. Therefore, the blower 7, the intake hole 16, and the exhaust hole 21 of this embodiment cooperate with each other to constitute a cooling mechanism for cooling the first temperature sensor stack 33 and the second temperature sensor stack 34.

Note that the configuration of the cooling mechanism is arbitrary, and the arrangement of the blower 7, the intake hole 16, and the exhaust hole 21 is also arbitrary. Further, the intake and exhaust directions may be reversed. Further, the type of the blower 7 is not particularly limited, and may be a general fan or a micro-blower using a piezoelectric element. Alternatively, if there is no problem in the measurement time during successive measurements in practical use, the cooling mechanism itself may be omitted.

The specific configurations in the embodiment above are described as an example, and the invention disclosed in this specification is not limited to those specific configurations themselves. Various modifications may be made to the disclosed embodiment by a person skilled in the art. For example, the shape, number, and arrangement of each member or a part thereof may be appropriately changed, and it is intended that the technical scope of the invention disclosed in this specification cover all such modifications.

The invention claimed is:

1. A contact type internal thermometer, comprising:
   a measurement surface that is brought into contact with a surface to be measured of a measurement object so as to calculate an internal temperature of the measurement object;
   a first temperature sensor stack comprising a first measurement surface side temperature sensor arranged on a measurement surface side of a first flexible printed board, and a first back surface side temperature sensor arranged on a back surface side of the first flexible printed board;
   a second temperature sensor stack comprising a second measurement surface side temperature sensor arranged on a measurement surface side of a second flexible printed board, and a second back surface side temperature sensor arranged on a back surface side of the second flexible printed board; and
   a controller configured to calculate the internal temperature of the measurement object based on measurement results of the first measurement surface side temperature sensor, the first back surface side temperature sensor, the second measurement surface side temperature sensor, and the second back surface side temperature sensor,
   wherein the first back surface side temperature sensor and the second back surface side temperature sensor have different surface areas such that one of the surface areas is intentionally larger than the other surface area.

2. The contact type internal thermometer according to claim 1, wherein the first back surface side temperature sensor and the second back surface side temperature sensor have different volumes such that one of the volumes is intentionally different from the other volume.

3. The contact type internal thermometer according to claim 1, wherein the first back surface side temperature sensor has an intentionally larger volume than a volume of the first measurement surface side temperature sensor.

4. The contact type internal thermometer according to claim 1, further comprising;
   a controller activates a cooling mechanism to cool the first temperature sensor stack and the second temperature sensor stack after the controller calculates an internal temperature.

5. The contact type internal temperature thermometer according to claim 4, wherein the cooling mechanism comprises:
   a blower;
   an intake port; and
   an exhaust port;
   wherein the blower is configured to draw external air through the intake port and cause air to be exhausted through the exhaust port.

\* \* \* \* \*